United States Patent [19]

Biollaz et al.

[11] 4,172,075
[45] Oct. 23, 1979

[54] FLUORO-STEROIDS AND PROCESSES FOR THEIR MANUFACTURE

[75] Inventors: Michel Biollaz, Basel; Jaroslav Kalvoda, Binningen, both of Switzerland

[73] Assignee: Ciba-Geigy Corporation, Ardsley, N.Y.

[21] Appl. No.: 879,413

[22] Filed: Feb. 21, 1978

Related U.S. Application Data

[63] Continuation of Ser. No. 704,900, Jul. 13, 1976, abandoned.

[51] Int. Cl.² .................... C07J 71/00; C07J 1/00; C07J 5/00
[52] U.S. Cl. .................... 260/239.55 D; 260/397.45; 260/397.5
[58] Field of Search ................ /Steroids MS File; 260/239.55 D, 397.45, 397.5

[56] References Cited

U.S. PATENT DOCUMENTS

| | | | |
|---|---|---|---|
| 3,033,749 | 5/1962 | Wettstein et al. | 260/397.45 X |
| 3,621,014 | 11/1971 | Stache et al. | 260/239.55 |
| 3,817,988 | 6/1974 | Barton et al. | 260/239.55 C |

OTHER PUBLICATIONS

Euw et al., Helv. Chim. Acta, 29, pp. 654-670, (1946).
Immer et al., Helv. Chim. Acta, 45, pp. 753-770, (1962).

Primary Examiner—Ethel G. Love
Attorney, Agent, or Firm—Theodore O. Groeger

[57] ABSTRACT 11,12-Unsaturated 9α-fluorosteroids comprising a new class of steroid compounds are obtained by a novel process, wherein a corresponding 9α-fluoro-11β-hydroxysteroid is dehydrated with a reagent of the formula $F_3SX$ in which X denotes an amino group derived from a secondary amine. Of a particular interest among the products of the invention are compounds of the general formula IB

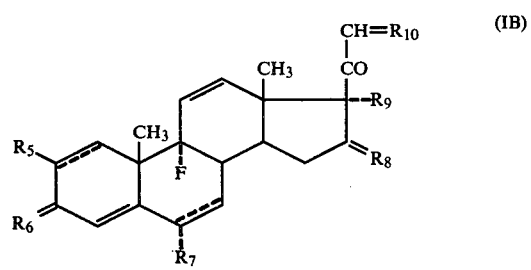

in which the symbols $R_5$–$R_{10}$ have the meanings given hereinafter; such compounds are especially useful as analogues of cortical hormones possessing antiinflammatory activity.

18 Claims, No Drawings

FLUORO-STEROIDS AND PROCESSES FOR THEIR MANUFACTURE

This is a continuation of application Ser. No. 704,900, filed on July 13, 1976, now abandoned.

The present invention relates to the hitherto unknown group of compounds comprising the 11,12-unsaturated 9α-fluorosteroids and to processes for their manufacture. In particular, the invention relates to the compounds of the general formula I

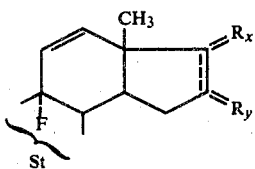

wherein St represents the remaining part of the steroid skeleton, which is optionally substituted and/or otherwise modified, $R_x$ denotes an optionally ketalised oxo group, an optionally substituted lower alkylidene radical, an optionally etherified or esterified hydroxyl group together with a hydrogen atom or an optionally substituted lower aliphatic hydrocarbon radical, or denotes a hydrogen atom together with an optionally substituted lower alkyl radical and $R_y$ denotes a lower alkylidene radical, an optionally etherified or esterified hydroxyl group together with a hydrogen atom, a lower alkyl radical together with a hydrogen atom or, in particular, two hydrogen atoms, it being possible for a 16,17-double bond to be present in place of one of the said hydrogen atoms in radical $R_x$ and one of the said hydrogen atoms in radical $R_y$, and to processes for the manufacture of these compounds.

Wherever it occurs in connection with an organic radical, the term "lower" signifies an organic radical which has at most 7, but preferably 1 to 4, carbon atoms.

The radical St consists of the ring A (carbon atoms C-1 to C-5 and C-10) and the remaining carbon atoms of ring B (C-6 and C-7) and carries the angular methyl group (C-19) in the 10-position It can also be otherwise modified, for example have a structure with expanded or contracted rings such as the A-Nor structure or A-Nor-B-homo structure and/or exhibit ring bridging for example the 3α,5-cyclo linkage. The rings A and B can, with respect to one another, assume the 5α- or 5β-configuration. The radical St can contain one, two or several double bonds, such as in the 1,2-, 2,3-, 3,4- and 6,7-positions, but above all in the 4,5- or 5,6-positions. The radical St can also be substituted by free, etherified and, in particular esterified hydroxyl groups, for example in the 3- and/or 19-positions and above all in the 3β-position, by free or ketalised oxo groups, especially in the 3-position, by lower alkyl radicals, for example in the 7α- or, in particular, the 6α-position, or by halogen atoms, such as bromine or, in particular, chlorine or fluorine atoms, especially in the 2-position and/or, above all, in the 6α-position.

A lower alkyl radical is, for example, an n-propyl, i-propyl, n-butyl, i-butyl, sec-butyl or tert-butyl radical or a branched or, preferably, straight-chain pentyl, hexyl or heptyl radical but above all an ethyl or methyl radical. A lower aliphatic hydrocarbon radical is a lower alkyl radical, for example one of those already mentioned, or a corresponding radical which also contains one or two multiple bonds, that is to say double bonds or acetylene bonds, such as, for example, a lower alkenyl, lower alkinyl and allenyl radical, for example a vinyl, allyl, methallyl, propargyl, hexadiinyl and, above all, ethinyl radical. A lower alkylidene radical is a radical which corresponds to the abovementioned lower alkyl radicals or lower alkenyl radicals and is divalent on one carbon atom, such as an ethylidene or isopropylidene radical and above all a methylene radical, or a vinylidene radical.

The lower aliphatic hydrocarbon radical already discussed and, optionally, also the lower alkylidene radical can be substituted by one or more identical or different substituents, which are located, above all, in the α-position and/or β-position (corresponding to the 20-position and 21-position respectively in steroid numbering). Possible substituents are halogen atoms, for example chlorine and fluorine, optionally etherified and, in particular, esterified hydroxyl groups, optionally ketalised oxo groups and optionally esterified carboxyl groups, it being possible for the carboxyl groups also to be in the form of their salts, especially their alkali metal salts. An esterified carboxyl group is to be understood, above all, as a carboxyl group which is in the form of its ester, in particular one of its esters with lower alkanols, but also as a carboxyl group which, together with a suitably distant hydroxyl group, which is present as a substituent, closes a 6-membered or, in particularly, 5-membered lactone ring.

A ketalised oxo group is derived, in particular, from lower alkanols, for example from methanol or ethanol, or, preferably, from α- or β-lower alkanediols, for example, 1,2- or 1,3-propanediol, or, above all, ethylene glycol; however, it can also be derived from the corresponding sulphur analogues of the said alcohols and contain sulphur atoms in place of one or both of the oxygen atoms.

An etherified hydroxyl group is derived, in particular, from a lower alkanol, preferably a straight-chain lower alkanol, for example methanol, ethanol, propanol and butanol, from an aryl-lower alkanol, preferably a phenyl-lower alkanol, for example benzyl alcohol or triphenylmethylcarbinol, or from an oxygen-containing heterocyclic alcohol, for example 2-tetrahydropyranol or 2-tetrahydrofuranol. Formally, it can, however, also be derived from a 1-lower alkoxy-lower alkanol, for example 1-butoxyethanol; the 1-butoxyethoxy group may be mentioned as an example of an etherified hydroxyl group of this type. In respect of the general sense, a hydroxyl group, such as that present in an acetalised or ketalised vicinal steroid diol, for example a 16α,17α-diol, is also to be regarded as an etherified hydroxyl group. The non-steroid structural component, which always links two such vicinal etherified hydroxyl groups, is preferably a lower aliphatic, cycloaliphatic or arylaliphatic ketone, for example acetone, cyclopentanone, cyclohexanone, acetophenone or benzophenone, or an aldehyde, for example formaldehyde. The 17α,20;20,21-bis-methylenedioxy grouping may also be mentioned as a special case of etherified hydroxyl groups.

An esterified hydroxyl group is derived, in particular, from an inorganic oxygen-containing acid, for example from one of the sulphuric or phosphoric acids, or, preferably, from an organic acid, for example from a sulphonic acid, for example from an aromatic sulphonic acid, such as benzenesulphonic acid, toluenesulphonic acid or p-bromobenzenesulphonic acid, or from an alkanesulphonic acid, such as methanesulphonic acid, or, in particular, from a carboxylic acid. A lactonised hydroxyl group is also to be regarded as an esterified hydroxyl group. From its mode of formation and certain substitution reactions, a halogen atom, for example an iodine or bromine atom and, in particular, a chlorine or fluorine atom, is also to be understood, especially when it is in the 21-position, as a special case, which nevertheless falls into this category, of a hydroxyl group esterified by a strong acid, that is to say a hydroxyl group esterified by hydriodic acid, hydrobromic acid, hydrochloric acid or hydrofluoric acid.

Acids which are possible as the carboxylic acid component of an esterified hydroxyl group are, above all, the carboxylic acids customary in steroid chemistry, including those in the form of the corresponding orthocarboxylic acids, for example monocarboxylic acids with at most 18 carbon atoms, such as aliphatic carboxylic acids and orthocarboxylic acids, in particular formic acid or orthoformic acid or a lower alkane-carboxylic acid or -orthocarboxylic acid in which the lower alkyl radical is one of those mentioned above, especially propionic acid, butyric acid, isobutyric acid, valeric acid, isovaleric acid, oenanthic acid and diethylacetic acid and, above all, caproic acid, trimethylacetic acid and acetic acid, but also corresponding halogenated lower alkanecarboxylic acids, such as chloroacetic acid and tri- chloro- or trifluoro-acetic acid, and also caprylic acid, pelargonic acid, capric acid, lauric acid, myristic acid, palmitic acid and stearic acid, undecylic and undecylenic acids, elaidic acid and oleic acid; cycloaliphatic or cycloaliphatic-aliphatic monocarboxylic acids, for example cyclopropanecarboxylic acid, cyclobutanecarboxylic acid, cyclopentanecarboxylic acid and cyclohexanecarboxylic acid and cyclopropylmethanecarboxylic acid or cyclobutyl-methanecarboxylic acid and a cyclopentyl-ethanecarboxylic acid or cyclohexyl-ethanecarboxylic acid; aromatic carboxylic acids, for example benzoic acids or orthobenzoic acids which are optionally substituted by fluorine, chlorine, bromine, hydroxyl, lower alkoxy, lower alkyl or nitro groups; aryl- or aryloxy-lower alkanecarboxylic acids and their analogues which are unsaturated in the chain, for example phenylacetic and phenoxyacetic acids, phenylpropionic acids and cinnamic acids, which are optionally substituted as indicated above for benzoic acid; and heterocyclic acids, for example furane-2-carboxylic acid, 5-tert.-butylfurane-2-carboxylic acid, 5-bromofurane-2-carboxylic acid, thiophene-2-carboxylic acid, nicotinic acid or isonicotinic acid or 3-(4-pyridyl)-propionic acid, and pyrrole-2- or -3-carboxylic acids which are optionally substituted by lower alkyl radicals, but also corresponding dicarboxylic acids with at most 12 carbon atoms, for example succinic acid, glutaric acid, adipic acid and phthalic acid and also corresponding α-aminoacids, in particular α-amino-lower alkanecarboxylic acids, preferably those in the naturally occurring configuration, for example glycine, proline, leucine, valine, tyrosine, histidine and asparagine, and also glutamic acid and aspartic acid.

When they are in a favourable position, for example when they are separated from one another by two or three carbon atoms, two hydroxyl groups can, together with one molecule of an orthocarboxylic acid form cyclic esters, such as, in particular, in the case of orthoesters of lower aliphatic ortho-acids and 17α,21-dihydroxypregnane compounds. The third oxygen atom of the ortho-acid functional group is usually occupied by the radical of a lower alkanol, above all by methyl or ethyl. Ortho-esters of orthocarbonic acid with 17α,21-dihydroxypregnane compounds are formed in an analogous manner; in this case the central carbon atom also carries two lower alkoxy groups.

The new 11,12-unsaturated 9α-fluorosteroids according to the invention can be used as intermediate products for the synthesis of valuable pharmaceutically active compounds, especially for hormone therapy and for fertility control, and also an additive in feedstuffs. Several of these steroids for example the compounds singled out in particular further below, at the same time themselves exhibit a biological action and, accordingly, can be used direct as active compounds in the abovementioned fields of application.

The 11,12-unsaturated 9α-fluoro-steroids according to the invention are obtainable by a chemically novel general process, which is characterised in that a 9α-fluoro-11β-hydroxy-steroid, in which any carboxyl groups and hydroxyl groups which may be present are preferably temporarily protected, is reacted with a compound of the formula $F_3SX$, wherein X denotes an amino group derived from a secondary amine.

Compounds of the general formula

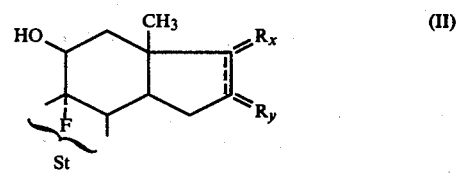

(II)

wherein St, $R_x$ and $R_y$ have the abovementioned meanings and any other hydroxyl groups and carboxyl groups which may be present are preferably in the esterified form, are preferred as starting materials.

Within the scope of the end products of the Formula I, the resulting products are, if desired, converted into one another in a manner which is in itself known, for example by liberating protected functional groups, such as, above all, esterified carboxyl groups and esterified hydroxyl groups, or by liberating the dihydroxyacetone side chain from the 17α, 20:20,21-bis-methylenedioxy grouping. Further conversions customary in steroid chemistry can also be carried out; in particular, hydroxyl groups can be esterified or etherified, eliminated or oxidised to oxo groups, oxo groups can be ketalised or reduced to hydroxyl groups, optionally with simultaneous introduction of a hydrocarbon radical, and/or further double bonds can be introduced into the resulting compounds. These subsequent conversions can be carried out independently or in appropriate combinations.

The process according to the invention is very surprising because the reactant of the formula $F_3SX$ which is used has hitherto served only for the purpose of fluorination by replacement of an oxygen grouping by fluorine, compare L.N. Markovskij, V.E. Pashissnik and A.V. Kirsanov: Synthesis 1973 (December), 787–789. The formation of the 11,12-double bond by elimination of a hydroxyl group in the 11-position is also surprising because this has been observed only as an exceptional case, compare C. Djerassi: Steroid Reactions, pages 227–266 and the literature sources cited there, and only in the case of distantly related compounds.

The process according to the invention proceeds readily even under very mild reaction conditions, so that other functional groups usually remain unaffected.

However, it is recommended that any carboxyl groups which may be present in the starting materials of the formula II should be in an esterified form to protect them against conversion into an acid fluoride.

With the exception of the 11β-hydroxyl group, which is to be reacted, any hydroxyl groups which may be present in the starting materials of the formula II should also be in a protected form, such as an etherified or, preferably, esterified form, during the reaction. Readily hydrolysable etherified hydroxyl groups, for example tetrahydropyranyloxy groups, and ketalised oxo groups can be split hydrolytically, in the course of the dehydration reaction or during processing of the reaction mixture, to give free hydroxyl groups and oxo groups respectively. However, for adequate protection of the dihydroxyacetone side chain it suffices when one of the two hydroxyl groups is esterified by a carboxylic acid which contains at least three carbon atoms, such as one of the abovementioned acids, above all propionic acid, butyric acid or trimethylacetic acid. A protective group of such a size already suffices to keep the reagent away from both the hydroxyl groups, that is to say both the esterified hydroxyl group and the free hydroxyl group. Of course, the dihydroxyacetone side chain can be in the form of a 17α,20;20,21-bis-methylenedioxy grouping. (The term "dihydroxyacetone side chain" is understood to mean the 17α,21-dihydroxy-20-oxo-pregnane grouping). The groupings mentioned can subsequently be converted into the desired free groups in a known manner, for example by hydrolysis.

The reactant (dehydrating agent) of the formula $F_3SX$ is a disubstituted amino-sulphur trifluoride, that is to say an amino-sulphur trifluoride in which the nitrogen atom is bonded to the sulphur atom and two carbon atoms. Accordingly, the substituents of the amino group are two identical or different open-chain or carbocyclic, optionally aromatic, hydrocarbon radicals, especially lower alkyl radicals, for example those mentioned above, or phenyl radicals, and the two radicals can be linked to one another by a simple C—C bond, by an oxygen bridge or by a lower alkylated nitrogen atom. The amino group designated by X is preferably a di-lower alkylamino group or lower alkyl-phenyl-amino group, such as the dimethylamino, methylethylamino, methylpropyl-amino, methyl-phenyl-amino, ethyl-propyl-amino, ethyl-phenyl-amino, dipropylamino, diisopropylamino or dibutylamino group, or an optionally C-lower alkylated pyrrolidino, piperidino, morpholino or N'-lower alkylpiperazino group, such as a N'-methylpiperazino group, and symmetrical amino groups are particularly preferred. Above all, this amino group is the diethylamino group and the corresponding fluorinating agent is diethylaminosulphur trifluoride.

The reaction according to the invention is optionally carried out in the presence of inert solvents or mixtures thereof. The reaction temperature depends on the specific properties of each particular reaction mixture and generally is between −20° and 80° and preferably 0° and 30°; advantageously, the reaction is carried out at room temperature.

The inert solvents used are those which do not, under the reaction conditions employed, react irreversibly either with the reactants or with the products. In particular, the following solvents can be used: carbocyclic hydrocarbons, for example saturated carbocyclic hydrocarbons, such as cyclopentane, cyclohexane, cycloheptane and decahydronaphthalene, or aromatic carbocyclic hydrocarbons, such as benzene, toluene or xylenes, which can also be halogenated in the nucleus, such as chlorobenzene, dichlorobenzenes, bromobenzene or fluorobenzene, and, in particular, aliphatic saturated hydrocarbons, preferably those which are liquid under atmospheric pressure and at room temperature, such as pentanes, hexanes, heptanes and octanes, or those which are halogenated, and in particular chlorinated, such as chloroform, 1,1- or 1,2-dichloroethane, 1,1-, 1,2- or 1,3-dichloropropane and, above all, dichloromethane. Further solvents which can be used are aliphatic and, in particular, cyclic ethers, such as diethyl ether, diisopropyl ether, ethylene glycol dimethyl ether, tetrahydrofurane and, above all, dioxane, and also nitrogen-containing, aromatic heterocyclic compounds, such as pyridine and its homologues or quinoline. It is optionally possible to use an excess of the fluorinating agent as the solvent and/or to combine several of the said solvents with one another.

The subsequent liberation of the protected oxygen-containing functional groups in the resulting process products is effected in a manner which is in itself known, preferably by hydrolysis. Etherified hydroxyl groups are preferably hydrolysed under the conditions of acid catalysis in the presence of an inorganic acid, for example sulphuric acid or a hydrogen halide acid, such as hydrochloric acid, hydrobromic acid or hydriodic acid, or of an organic acid, for example a sulphonic acid, such as p-toluenesulphonic acid or sulphosalicylic acid, or of a relatively strong carboxylic acid, such as oxalic acid or formic acid. Enol-ethers and ketals or acetals are also hydrolysed analogously to the corresponding oxo derivatives. Carbonyl-containing ester groups of various types, whether these be esterified hydroxyl groups, esterified carboxyl groups, enol-acylated oxo groups or lactone groups, can be hydrolysed under acid conditions; preferably, however, they are hydrolysed by means of base catalysis. The basic catalysts used are preferably hydroxides, carbonates or bicarbonates of the alkali metals, especially of sodium or potassium. As is known, it is also possible, by suitable choice of the reactants and conditions, selectively to liberate individual hydroxyl groups, for example of the two esterified hydroxyl groups in a 17α,21-ortho-ester to liberate only that in the 21-position, the hydroxyl group in the 17α-position remaining as a normal esterified hydroxyl group. Esterified hydroxyl groups can also be liberated by reduction, for example by the action of an ester-reducing agent, such as a complex hydride or diborane.

The subsequent esterification or etherification of hydroxyl groups in the resulting compounds is also effected in a manner which is in itself known. For esterification, the compound to be esterified is, for example, treated with an excess of the acid itself, such as with formic acid, or with a reactive derivative thereof, for example with a derivative of one of the abovementioned acids, and in particular with an anhydride or acid halide, advantageously in the presence of a tertiary base, such as pyridine, quinoline or N-ethylpiperidine. Hydroxyl groups which are difficult to esterify, for example a tertiary 17α-hydroxyl group, can advantageously be esterified with an acid anhydride under the catalytic action of organic sulphonic acids, for example benzenesulphonic acid, p-toluenesulphonic acid, salicylsulphonic acid or camphorsulphonic acid. In order to form ortho-esters, especially those derived from 17α,21-dihydroxy compounds, the reaction is carried out in a known manner under the conditions of transesterification, for example in such a way that a suitable compound containing a free dihydroxyacetone side chain is treated with an excess of the desired orthocarboxylic acid ester, for example triethyl orthopropionate, in the presence of a strong acid. Advantageously, provision is made for the removal of the volatile lower alkanol which is liberated.

For etherification, the compounds to be etherified are, for example, treated with reactive derivatives of alcohols, for example with esters of strong acids, such as halides, sulphates or sulphonic acid esters, possible alcohol components being, in particular, one of the abovementioned alcohols. The reaction is preferably carried out in the presence of basic agents. In order to form tetrahydropyranyl ethers and analogous ethers, a corresponding unsaturated derivative, such as 2,3-dihydropyrane or a vinyl lower alkyl ether, for example vinyl butyl ether, is preferably used as the reagent and the reaction is carried out under the conditions of acid catalysis, preferably in the presence of an organic sulphonic acid.

The esterification of carboxyl groups, which is optionally to be carried out, is also effected in a manner which is in itself known. For example, the carboxylic acid to be esterified is treated with an excess of an alcohol, in particular one of those mentioned above, in the presence of an acid catalyst, for example a strong inorganic acid, or the free acid is first converted into its reactive derivative, such as the chloride or anhydride, and the latter is reacted with the desired alcohol. Lower alkyl esters, and above all methyl esters, can also advantageously be manufactured by reacting the free carboxylic acid, to be esterified, with the corresponding diazolower alkane, above all diazomethane. The lactonisation of a carboxyl group usually takes place spontaneously when a carboxyl group present as a salt is liberated by acidification; lactonisation can also be accelerated by acid catalysis and/or by using dehydrating agents, such as acetic anhydride, anhydrous copper sulphate or molecular sieves or by azeotropic distillation.

Ketalisation, enol-acylation and the formation of enol-ethers, which are optionally to be carried out, in particular in order to protect the oxo groups, are also effected in a manner which is in itself known, in particular under the conditions of acid catalysis and optionally employing dehydrating agents or azeotropic distillation. For ketalisation, lower alkanols, such as methanol or ethanol, and in particular $\alpha$- and $\beta$-glycols, such as 1,2- or 1,3-propanediol and 1,2- or 2,3-butanediol, and, above all, ethylene glycol, or reactive derivatives of these alcohols, such as acetals or ketals, especially those in which the carbonyl component is readily volatile, such as, for example, 2,2-dimethyl-1,3-dioxolane, are used, for example. Analogous thioketals are obtained in an analogous manner, but starting from the sulphur analogues of the abovementioned alcohols and above all from 1,2-ethanedithiol or a reactive derivative.

In an analogous manner, vicinal steroid-diols are reacted with non-steroid ketones and aldehydes, this being the case, for example, when forming ketals, for example acetonides, or acetals from 16$\alpha$,17$\alpha$-diols or when converting 17$\alpha$,21-dihydroxy-20-oxo-pregnanes to corresponding 17$\alpha$,20;20,21-bis-methylenedioxy derivatives using formaldehyde. In place of a free 16,17-diol, it is also possible to use a corresponding ester, especially a 16-monoester; the intermediate liberation of the diol then takes place under the reaction conditions of the ketalisation or acetalisation and the addition of a lower alkanol to the reaction mixture facilitates this liberation. In place of the free carbonyl compound it is also possible to use a reactive derivative thereof, for example an acetal or ketal, derived from a readily volatile alkanol, especially methanol or ethanol, or an enol-acylate, for example an enol-acetate, such as isopropylidene acetate, or a mixture of the free ketone and such a derivative. In the case of aldehydes, their oligomers, for example trimers, such as paracetaldehyde, can, moreover, also be used. The reagent used for the formation of the enol-ethers is preferably an ortho-ester of a lower alkanol, especially of methanol or ethanol, and a lower aliphatic carboxylic acid, especially formic acid; particularly preferred reagents are methyl orthoformate and, above all, ethyl orthoformate. In the presence of the dihydroxyacetone side chain, however, the possibility of simultaneous formation of the 17$\alpha$,21-ortho-ester must be taken into account. Enol-acylation is advantageously carried out by reaction with a reactive derivative of the desired carboxylic acid with acid catalysis; preferably, an anhydride, such as acetic anhydride, is used as the reagent and an organic acid, such as benzenesulphonic acid, p-toluenesulphonic acid, salicylsulphonic acid or camphorsulphonic acid, is used as the catalyst. Ketenes, and especially an unsubstituted ketene, can also be used as reactive carboxylic acid derivatives. In the case of an oxo group conjugated with a double bond, the formation of the ketal, enol-ether or enol-ester can be accompanied by a shift of the double bonds, for example in the case of the 3-oxo-$\Delta^4$-grouping, the 4,5-double bond migrates into the 5,6-position.

In resulting process products, free hydroxyl groups can also be oxidised to oxo groups in a manner which is in itself known. Preferred oxidising agents for secondary hydroxyl groups are considered to be compounds of 6-valent chromium, such as chromium trioxide and chromic acid and its alkali metal salts, and, advantageously, lower alkanecarboxylic acids, such as acetic acid or propionic acid, or pyridine or acetone, optionally diluted with a halogenated lower alkane, such as dichloromethane or chloroform, and/or in the presence of aqueous sulphuric acid, are used as the reaction medium. The primary 19-hydroxyl group is also oxidised in an analogous manner; in this reaction, the 10-carboxaldehyde group is formed under relatively mild reaction conditions or the 10-carboxyl group is formed when the reaction is carried out under more vigorous conditions. Another preferred alternative for the oxidation of the secondary hydroxyl group is Oppenauer oxidation, that is to say oxidation with a ketone, such as acetone or cyclohexanone, under the catalytic action of an aluminium lower alkoxide, such as aluminium isopropylate. An allylic hydroxyl group, that is to say a hydroxyl group alongside a double bond, such as, for example, the hydroxyl group in a 3$\beta$-hydroxy-4-ene compound, can, in a manner which is in itself known, be oxidised by manganese dioxide to the corresponding oxo group. This reaction, which takes place readily, is particularly advantageous when an $\alpha,\beta$-unsaturated oxo group which has also been reduced during the reduction of another oxo group, is to be regenerated.

The primary 21-hydroxyl group can also be oxidised to the oxo group in a manner which is in itself known, for example by the action of atmospheric oxygen in the presence of a copper-II salt, such as copper acetate. It is also possible to use an indirect procedure such that a 21-hydroxy compound is treated with tosyl chloride (or an equivalent sulphonic acid derivative) in pyridine or a similar tertiary base, the intermediate product of the partial formula

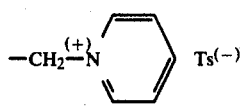

is subjected to a condensation reaction with nitrosodimethylaniline to give a nitrone of the partial formula

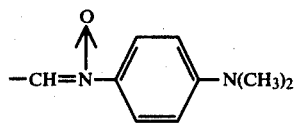

and this is hydrolysed with water with acid catalysis. The acid-catalysed rearrangement of the dihydroxyacetone side chain to the 20,21-dioxo-pregnane grouping unsubstituted in the 17-position is a special case of the formation of the 21-aldehyde group. Depending on the solvent used (for example water, an alkanol or alkanediol or a carboxylic acid), the terminal aldehyde group is obtained as a hydrate, a hemiacetal, an acetal or acylal or in a tautomeric form thereof. A hydroxyl group in the 21-position in the dihydroxyacetone side chain can also be eliminated in a manner which is in itself known by converting it into a hydroxyl group esterified with a strong acid, and removing this by reduction, for example with zinc in acetic acid, with sodium bisulphite or, preferably, with sodium iodide in acetic acid. Suitable ester-forming strong acids, which may be mentioned are organic sulphonic acids, especially toluenesulphonic acid and very particularly methanesulphonic acid, and also hydrogen halide acids, especially hydrobromic acid and above all hydriodic acid. The elimination of a 21-iodide with sodium bisulphite in ethanol is particularly advantageous.

In resulting process products, it is also possible to reduce oxo groups, especially the 3-oxo group and above all the 17-oxo group, to hydroxyl groups. The reduction is carried out in a manner which is in itself known; reagents advantageously used for this purpose are diborane or complex hydrides, especially those of aluminum or boron and an alkali metal or alkaline earth metal, such as, for example, sodium aluminium hydride, calcium borohydride and lithium borohydride, but especially lithium aluminium hydride and above all sodium borohydride, or their derivatives in which one or more hydrogen atoms have been replaced by lower alkoxy radicals, such as methoxy-sodium borohydride and, in particular, tri-tert.-butoxy-lithium aluminium hydride. The choice of the solvent and of the conditions for the reduction depends on the reducing agent used and is in accordance with the generally known principles. In the case of a selective reduction, for example that of the 17-oxo group, the other oxo groups are temporarily protected as ketals or enol-esters or enol-ethers and, when a 3-oxo-$\Delta^4$-grouping is present, it is also possible so to proceed that this grouping is also reduced and then selectively dehydrogenated, for example with manganese dioxide, back to the 3-oxo-$\Delta^4$-grouping.

However, the reduction of the oxo groups, and above all of the 17-oxo group, can also be carried out in a manner which is in itself known, with simultaneous introduction of a hydrocarbon radical, and especially of a lower aliphatic hydrocarbon radical, for example one of those mentioned initially, by reacting a corresponding oxo compound with a corresponding organometallic compound. When the hydrocarbon radical to be introduced is a lower alkyl radical, a Grignard compound, for example a lower alkyl-magnesium halide, such as methyl-magnesium bromide or methyl-magnesium iodide, or a lower alkyl-lithium, such as methyl-lithium, is preferred as the organometallic compound; when a 1-alkinyl radical, and especially the ethinyl radical, is to be introduced, it is advantageous to use a corresponding alkali metal compound, for example sodium acetylide or potassium acetylide or, in particular, lithium acetylide. In the latter case, it is particularly advantageous to use the lithium acetylide in the form of its complex with ethylenediamine. In these reactions, the other oxo groups must be protected in a manner analogous to that described above for the case of selective reduction. When the oxo group to be reacted is combined with one or two adjacent double bonds to form a conjugated system, such as is the case, for example, in the 3-oxo-4,6-diene grouping, it is possible to carry out the reaction with a Grignard compound, especially a methyl-magnesium halide, in a known manner, and in particular in the presence of a copper-I salt, in such a way that the hydrocarbon radical to be introduced is introduced, not on the carbon atom which carried the oxo group, but on the carbon atom at the end of the conjugated system and, formally, this corresponds to a 1,4- or 1,6-addition. In this reaction the oxo group is converted to a hydroxyl group, but this is then in an enol grouping and, during working up, rearranges to form an oxo group, with formal saturation of the C—C double bond. The 7α-methyl-3-oxo-4-ene grouping then results from the conjugated system mentioned above by way of example.

It is also possible to introduce double bonds into the resulting end products in a manner which is in itself known. For example, $\Delta^4$-3-oxo compounds, optionally in the form of their 3-enol-acylates or 3-enol-ethers, can be reacted with quinones, such as chloranil or, in particular, 2,3-dichloro-5,6-dicyano-1,4-benzoquinone, and, depending on the choice of the reaction conditions, which are in themselves known, this results in the formation of a 6,7- and/or 1,2-double bond.

The 1,2-dehydrogenation of $\Delta^4$-3-ketones can also be achieved in a manner which is in itself known by treatment with selenium dioxide, or microbiologically, for example by means of the micro-organisms Corynebacterium simplex or Septomyxa affinis; 6,7-dehydrogenation is also achieved by reacting an enol-ether of a $\Delta^4$-3-ketone with manganese dioxide.

Amongst the 11,12-unsaturated 9α-fluoro-steroids which are obtainable according to the process, the compounds of the general formula IA

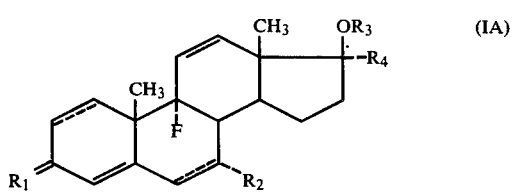

wherein $R_1$ denotes an oxo group, a hydrogen atom together with an esterified or free hydroxyl group, or two hydrogen atoms, $R_2$ denotes a hydrogen atom or the methyl group, $R_3$ denotes a hydrogen atom or, conjointly with the oxygen atom, denotes a hydroxyl group, especially a hydroxyl group etherified by a lower alkanol or a cycloaliphatic alcohol, such as cyclopentanol or cyclohexanol, or a hydroxyl group esterified by a carboxylic acid, preferably an aliphatic carboxylic acid with 2 to 12 carbon atoms, and $R_4$ denotes a hydrogen atom or a lower aliphatic hydrocarbon radical, or $R_3$ and $R_4$ conjointly represent a valency bond, and an additional double bond can be present in both the 1,2-position and/or the 6,7-position, are of particular interest because of their advantageous biological properties. These compounds are distinguished, in particular, by their sex hormone-like pharmacological properties. On the one hand they have a central action in that they block the secretion of pituitary gonadotrophins and on the other hand they also have a peripheral influence both on the male and on the female sexual functions, as can be demonstrated by the customary animal experiments. Accordingly, they possess very valuable anabolic, androgenic, progestative, anti-androgenic, antioestrogenic, ovulation-inhibiting and gonad-inhibiting activities. Because of their peripheral fertilisation-inhibiting properties, for example the contraceptive effect on the transport of the ovum and/or the cervical mucus, and their antinidation activity they are of interest as contraceptives. Because of these favourable pharmacological properties, they can be used in corresponding specific indications in place of the known sex hormones and, for this purpose, they can be administered in the same way as the sex horomones, the relative activity being taken into account when determining the dosage. In addition, these compounds can serve as intermediate products for other compounds which belong to the same group of end products but have modified pharmacological properties, or can be used as valuable starting materials for compounds of other categories.

Amongst the compounds belonging to this group, those which are of particular importance, because of their androgenicanabolic properties, but also their antioestrogenic, antigestagenic and gonadotrophin-inhibiting properties, are those compounds of the general formula IA wherein $R_1$ is an oxo group, $R_2$ is a hydrogen atom and, very specifically, the methyl radical, $R_3$ is a hydrogen atom, lower alkyl, cycloalkyl with 5 or 6 ring members or alkanoyl with 2 to 12 carbon atoms and $R_4$ is a hydrogen atom or the methyl radical and these compounds can also carry a double bond in the 1,2-position. However, those compounds of the general formula IA wherein $R_1$ is two hydrogen atoms, a hydrogen atom together with a free hydroxyl group or, in particular, an oxo group, $R_2$ is a hydrogen atom, $R_3$ is lower alkanoyl or, in particular, a hydrogen atom and $R_4$ is an unsaturated hydrocarbon radical with 1–4 C atoms, especially the ethinyl radical, and which can also carry a double bond in the 1,2-position and/or, in particular, in the 6,7-position, also merit very particular attention. These compounds are also distinguished by their blocking action on the secretion of the gonadotrophins, but above all by their gestagenic, antioestrogenic, antiandrogenic and nidation-inhibiting action.

Compounds of the general formual IA are accessible from the corresponding 11β-hydroxy compounds by the general dehydration process according to the invention, with the proviso that any hydroxyl groups which may be present in the 3-position and the 17-position are in a protected form. If desired, the hydroxyl groups are subsequently liberated or free hydroxyl groups are formed from corresponding oxo groups in a manner which is in itself known, by subsequent reduction, preferably with a complex hydride. If desired, it is also possible subsequently to introduce the hydrocarbon radical $R_4$: in this case compounds of the formula IA wherein $R_3$ and $R_4$ conjointly represent a valency bond are used as the starting materials and the reaction is preferably carried out under the conditions described initially. If desired, it is also possible subsequently to introduce the lower alkyl radical into the 7α-position. If it is desired to obtain a compound of the formula IA which is unsaturated in the 1,2-position and/or the 6,7-position, it is also possible, in a manner which is in itself known, subsequently to introduce the desired double bonds into a corresponding compound which is saturated in these positions.

Compounds of the general formula IB

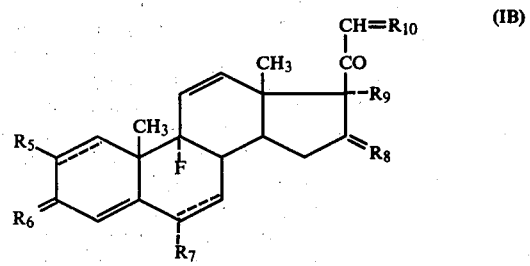

wherein $R_5$ is a hydrogen atom, an α-oriented methyl radical or, if a 1,2-double bond is present, a chlorine atom, $R_6$ is an oxo group or a hydrogen atom together with an optionally esterified hydroxyl group, $R_7$ is a hydrogen atom, the methyl radical or a halogen atom, $R_8$ is two hydrogen atoms, the methylene radical, a hydrogen atom together with an α- or β-oriented methyl radical or an α-oriented free hydroxyl group, $R_9$ is a hydrogen atom or an optionally esterified hydroxyl group and $R_{10}$ is two hydrogen atoms, an optionally hydrated or acetalised oxo group or a hydrogen atom together with an optionally esterified or etherified hydroxyl group, and in which a double bond can be present in both the 1,2-position and/or the 6,7-position and in which the 16α,17α-diol grouping which may be present, can be ketalised or acetalised by an oxo compound of the formula $R_{11}$—CO—$R_{12}$ in which $R_{11}$ and $R_{12}$ independently of one another denote a hydrogen atom, a lower alkyl radical, a phenyl radical or a benzyl radical or, conjointly, form the tetramethylene radical or pentamethylene radical, are also of particular interest. These compounds are distinguished by valuable horome-like properties and can therefore be used in place of the natural hormones, or their known analogues, in corresponding specific indications.

Those compounds of the general formula IB wherein $R_5$ is a hydrogen atom or, when a 1,2-double bond is present, a chlorine atom, $R_6$ is an oxo group, $R_7$ is a hydrogen atom, a methyl radical and, in particular, a fluorine atom, $R_8$ is two hydrogen atoms or one hydrogen together with a hydroxyl group in the α-position or with a methyl radical in the β-position or, in particular, the α-position, and $R_9$ and $R_{10}$ independently of one another are each a free hydroxyl group or an esterified hydroxyl group, especially a hydroxyl group esterified by a lower alkanecarboxylic acid, and in which a 1,2-double bond is preferably present, are particularly valuable as analogues of the hormones of the adrenal cortex. The 16,17-ketals, especially acetonides, cyclopentanonides, cyclohexanonides and acetophenonides of those compounds which have already been singled out and which have a hydroxyl group in both the 16α-position and the 17α-position are also preferred. Furthermore, the compounds of the formula IB wherein $R_5$, $R_6$, $R_7$ and $R_{10}$ have the preferred meanings already mentioned, $R_8$ denotes hydrogen together with a methyl group in the α-position and $R_9$ denotes hydrogen are also preferred. These compounds have a hormonal action which is analogous to the characteristic properties of the natural hormones of the adrenal cortex; the mineralo-corticoid properties, that is to say the influence on the equilibrium of sodium, potassium and water in the body tissues, and, above all, the antiinflammatory action are therapeutically especially valuable. Typical representatives of these preferred compounds are 9α-fluoro-17α,21-dihydroxypregna-4,11-diene-3,20-dione, 9α-fluoro-17α, 21-dihydroxy-16α-methyl-pregna-4,11-diene-3,20-dione, 9α-fluoro-17α,21-dihydroxy-16β-methyl-pregna-4,11-diene-3,20-dione, 6α,9α-difluoro-17α,21-dihydroxy-pregna-4,11-diene-3,20-dione, 6α,9α-difluoro-17α,21-dihydroxy-16α-methyl-pregna-4,11-diene-3,20-dione, 6α,9α-difluoro-17α,21-dihydroxy-16β-methyl-pregna-4,11-diene-3,20-dione, 9α-fluoro-17α,21-dihydroxy-6α-methyl-pregna-4,11-diene-3,20-dione, 9α-fluoro-17α,21-dihydroxy-6α,16α-dimethyl-pregna-4,11-diene-3,20-dione and 9α-fluoro-17α,21-dihydroxy-6α,16β-dimethyl-pregna-4,11-diene-3,20-dione and their 21-esters and/or 17-esters, especially their esters with lower alkanecarboxylic acids, above all with acetic acid, butyric acid, valeric acid and trimethylacetic acid; and also 9α-fluoro-17α,21-dihydroxy-pregna-1,4,11-triene-3,20-dione 9α-fluoro-17α,21-dihydroxy-16α-methyl-pregna-1,4,11-triene-3,20-dione, 9α-fluoro-17α,21-dihydroxy-16β-methyl-pregna-1,4,11-triene-3,20-dione, 6α,9α-difluoro-17α,21 -dihydroxy-pregna-1,4,11-triene-3,20-dione, 6α,9α-difluoro-17α,21-dihydroxy-16α-methyl-pregna-1,4,11-triene-3,20-dione, 6α,9α-difluoro-17α,21-dihydroxy-16β-methyl-pregna-1,4,11-triene-3,20-dione, 9α-fluoro-17α,21-dihydroxy-6α-methyl-pregna-1,4,11-triene-3,20-dione, 9α-fluoro-17α,21-dihydroxy-6α,16α-dimethyl-pregna-1,4,11-triene-3,20-dione and 9α-fluoro-17α,21-dihydroxy-6α,16β-dimethyl-pregna-1,4,11-triene-3,20-dione and especially the corresponding 2-chloro-analogues and 21-esters and/or 17-esters of all of these compounds, especially esters with lower alkanecarboxylic acids, above all with acetic acid, propionic acid, butyric acid, valeric acid and trimethylacetic acid, but also 9α-fluoro-21-hydroxy-16α-methyl-pregna-4,11-diene-3,20-dione, 9α-fluoro-21-hydroxy-16α-methyl-pregna-1,4,11-triene-3,20-dione, 9α-fluoro-21-hydroxy-6α,16α-dimethyl-pregna-4,11-diene-3,20-dione, 9α-fluoro-21-hydroxy-6α,16α-dimethyl-pregna-1,4,11-triene-3,20-dione, 6α,9α-difluoro-21-hydroxy-16α-methyl-pregna-4,11-diene-3,20-dione and 6α,9α-difluoro-21-hydroxy-16α-methyl-pregna-1,4,11-triene-3,20-dione and 21-esters of these compounds, preferably the preferred esters mentioned immediately above, and 9α-fluoro-16α,17α,21-trihydroxy-pregna-1,4,11-triene-3,20-dione and its 21-esters, preferably the preferred esters mentioned immediately above, and 16,17-ketals, especially acetonides, acetophenonides, cyclopentanonides and cyclohexanonides of the last-mentioned compounds.

Among the compounds of the general formula IB, those compounds wherein $R_5$ is a hydrogen atom, $R_6$ is an oxo group, $R_7$ is a chlorine atom or a fluorine atom, $R_8$ is a methylene group or, in particular, two hydrogen atoms, $R_9$ is a hydrogen atom or a free or esterified hydroxyl group, especially a hydroxyl group esterified with a lower alkanecarboxylic acid, and $R_{10}$ represents two hydrogen atoms, and wherein a double bond can be present, preferably in the 1,2-position and/or, especially, in the 6,7-position, are also of particular importance. These compounds are distinguished by their sex hormone-like properties, especially by their gestagenic, antioestrogenic, antiandrogenic and ovulation-inhibiting and nidatin-inhibiting properties; they can be employed wherever gestagens (that is to say progesterone-like hormones) are used as pharmaceutical formulations or contraceptives.

The advantageous biological properties of the compounds according to the invention can also be demonstrated on the following examples of several typical active compounds: thus, 9α-fluoro-17α,21-dihydroxy-16α-methyl-pregna-1,4,11-triene-3,20-dione 17,21-dipropionate displays a local antiinflammatory action, as can be demonstrated by the cottonwool granuloma test (on rats) using doses of 0.3 mg per pellet. The 16-epimeric compound, that is to say 9α-fluoro-17α,21-dihydroxy-16β-methyl-pregna-1,4,11-triene-3,20-dione 17-valerate-21-propionate, also displays an action of this type and of the same order of magnitude. A particularly outstanding activity can be determined both with 6α,-9α-difluoro-17α,21-dihydroxy-16α-methyl-pregna-1,4,11-triene-3,20-dione 17,21-dipropionate and with 6α,9α-difluoro-21-hydroxy-16α,17α-isopropylidenedixy-pregna-1,4,11-triene-3,20-dione 21-acetate; in the cottonwool granuloma test (on rats) both compounds display a marked local antiinflammatory action over the entire dosage range from 0.03 to 0.3 mg per pellet. In comparison with this excellent local action, the systemic action of these compounds is surprisingly slight. In the indicated dosage range, measured relative to the body weight, the weight of the adrenal gland and the weight of the thymus gland, no systemic action can be detected with 6α,9α-difluoro-17α,21-dihydroxy-16α-methyl-pregna-1,4,11-triene-3,20-dione 17,21-dipropionate, even at the highest dosage; 6α,9α-difluoro-21-hydroxy-16α,17α-isopropylidenedioxy-pregna-1,4,11-triene-3,20-dione 21-acetate also displays the first indications of systemic activity only at the highest test dose. This dissociation of the local and the systemic activity is particularly desirable because the latter is regarded as a troublesome side effect in most fields of therapeutic application.

The compounds of the formula IB, characterised above, are generally obtainable direct from the corresponding 11β-hydroxy-9α-fluoro compounds by the dehydration process according to the invention, with the proviso that the other free hydroxyl groups are protected in a suitable manner, for example by esterification. It is to be noted that, for adequate protection of the two hydroxyl groups in the 17α-position and the 21-position, it suffices if only one of the two hydroxyl groups is esterified with a carboxylic acid which contains at least 3 carbon atoms, such as propionic acid, butyric acid, valeric acid or trimethylacetic acid, and it is immaterial which of the two hydroxyl groups is so esterified. If compounds of the formula IB which contain free hydroxyl groups are desired, these are obtained by hydrolysis, preferably in the manner described initially, from the corresponding end products which contain these groups in an esterified or etherified form.

Conversely, it is also possible, in resulting compounds, subsequently to esterify free hydroxyl groups in a known manner or to ketalise or acetalise the 16α,17α-diol grouping. If desired, it is also possible to introduce a 1,2-double bond and/or a 6,7-double bond into a resulting compound which is saturated in the corresponding position; advantageously, the dehydrogenation methods mentioned initially are used for this purpose. If desired, the resulting compounds of the formula IB in which $R_{10}$ denotes a hydrogen atom together with a free hydroxyl group can be converted, in a manner which is in itself known and preferably as described initially, into corresponding compounds wherein $R_{10}$ represents two hydrogen atoms, or can be converted to compounds wherein $R_{10}$ represents an optionally hydrated, acetalised or ketalised oxo group. This last-mentioned conversion can optionally take place, as described initially, with elimination of a free 17α-hydroxyl group.

The compounds of the general formula IB wherein $R_{10}$ represents an optionally esterified hydroxyl group together with a hydrogen atom are advantageously obtained starting from the corresponding compounds of the formula IB wherein $R_{10}$ represents two hydrogen atoms, by halogenating these compounds in the 21-position in a manner which is in itself known, replacing the halogen atom, and in particular iodine, by an esterified hydroxyl group and optionally liberating the latter. The halogenation in the 21-position is preferably carried out by the action of elementary iodine in the presence of calcium oxide and, optionally, also calcium chloride. The subsequent replacement, by an esterified hydroxyl group, and especially by a lower alkanoyloxy group, of the halogen atom which has been introduced, is preferably effected by treatment with a salt of a corresponding acid, especially by means of an alkali metal salt or of a salt with an organic base, for example with a tertiary amine such as a tri-lower alkylamine. Potassium lower alkanoates and tri-lower alkyl-ammonium lower alkanoates, for example acetates, may be mentioned as being particularly advantageous for this reaction.

The compounds of the general formula IA and IB are also obtained when corresponding compounds in which one or more oxo groups are present in the form of a ketal, enol-ether or enol-acylate are hydrolysed in a manner which is in itself known, and in particular as described above.

The compounds of the formula IB wherein $R_9$ represents a free hydroxyl group and $R_{10}$ represents a hydrogen atom together with a free hydroxyl group are also obtained when a corresponding 17α,20;20,21-bis-methylenedioxypregnane compound is saponified. The preferred conditions for this reaction are considered to be those of acid-catalysed hydrolysis, for example by means of a dilute lower aliphatic carboxylic acid, such as formic acid or acetic acid, or by means of hydrofluoric acid, optionally in the presence of urea.

Depending on the choice of the procedure and of the starting materials, the new compounds according to the invention can be in the form of mixtures of isomers or racemates. This is the case, in particular, with compounds which have been manufactured by a totally synthetic route. Such mixtures of isomers, which may have been obtained can be separated into their individual components in a known manner, on the basis of the physical-chemical differences between the components, for example by chromatography and/or fractional crystallisation. Racemates which may have been obtained are first combined, in a manner which is in itself known, with an optically active compound, for example esterified with an optically active acid, and the mixture of isomers thus obtained is separated as indicated above. The individual antipodes are liberated from the individual components, thus obtained, in a manner which is in itself known, for example by hydrolysis.

The invention also relates to those embodiments of the above processes in which a compound obtainable as an intermediate product at any stage is used as the starting material and the missing steps are carried out or in which a starting material is formed under the reaction conditions.

The starting materials for the processes of the present invention are known or can be manufactured in a manner which is in itself known. Appropriately, those starting materials wich contain the substituents mentioned in particular above, and especially those which lead to the end products described in particular or singled out by formulae, are used.

The present invention also relates to the manufacture of pharmaceutical formulations and of contraceptives for humans and mammals, which formulations and contraceptives contain the new pharmacologically active compounds, described above, of the present invention as the active substances together with a pharmceutical excipient. The excipients used are organic or inorganic substances which are suitable for enteral, for example oral, or parenteral administration or for topical application. Substances which can be used as the excipients are those substances which do not react with the new compounds, such as, for example, water, gelatine, lactose, starch, magnesium stearate, talc, vegetable oils, benzyl alcohols, gum, polyalylene glycols, vaseline, cholesterol and other known medicinal excipients. The pharmaceutical formulations can be in a solid form, for example as tablets, dragées or capsules, or in a liquid or semi-liquid form, as solutions, suspensions, emulsions, ointments or creams. These pharmaceutical formulations are optionally sterilised and/or contain auxiliaries, such as preservatives, stabilisers, wetting agents or emulsifiers, salts for regulating the osmotic pressure or buffers. They can also contain yet further therapeutically valuable or biologically active compounds.

The invention is described in more detail in the examples which follow, without its scope being restricted as a result. The temperatures are given in degrees Centigrade.

EXAMPLE 1

0.12 ml of piperidinosulphur trifluoride are added to a solution, which is stirred under argon, of 160 mg of 9α-fluoro-11β,17β-dihydroxy-17α-methyl-androst-4-en-3-one 17-trifluoroacetate in 2 ml of absolute dioxane. The reaction mixtue is then stirred for 60 minutes at 25°, poured into a solution of sodium bicarbonate which is cooled with ice, and extracted with ethyl acetate. The organic solutions, which are washed with water until neutral and dried over sodium sulphate, give, after evaporation in a waterpump vacuum, a yellow amorphous crude product from which pure 9α-fluoro-17β-hydroxy-17α-methyl-androsta-4,11-dien-3-one 17-trifluoroacetate, which after crystallisation from acetone/hexane melts at 146°–147°, is obtained by chromatography on 60 times the amount by weight of silica gel, using hexane/ethyl acetate (4:1) as the eluant.

9α-Fluoro-11β,17β-dihydroxy-17α-methyl-androst-4-en-3-one 17-trifluoroacetate, which is used as the starting material and melts at 158°–159°, is obtained by selective trifluoroacetylation of 9α-fluoro-11β,17β-dihydroxy-17α-methyl-androst-4-en-3-one in dioxane/methylene chloride/pyridine by means of trifluoroacetic anhydride at −70°.

EXAMPLE 2

A solution of 11 g of sodium acetate in 9 ml of water is added to a solution of 7.2 g of 9α-fluoro-17β-hydroxy-17α-methyl-androsta-4,11-dien-3-one 17-trifluoroacetate in 150 ml of methanol and the mixture is boiled for 5½ hours in an argon atmosphere and evaporated under a waterpump vacuum. The residue is taken up in methylene chloride and water and the organic phase is washed with water, dried and evaporated. Free 9α-fluoro-17β-hydroxy-17-methyl-androsta-4,11-dien-3-one, which has a melting point of 181°–182° (from acetone/hexane); $[\alpha]_D = -4°$ (c=0.464; CHCl$_3$), is obtained by filtering a solution of the resulting brownish crude product in methylene chloride through 50 g of aluminum oxide (activity III).

EXAMPLE 3

1.8 ml of diethylaminosulphur trifluoride are added to a solution of 2.0 g of 9α-fluoro-11β,17α,21-trihydroxy-16α-methyl-pregna-1,4-diene-3,20-dione 17,20-dipropionate (Dexamethason 17,21-dipropionate) in 30 ml of dioxane in a glass flask, at 25° under a nitrogen atmosphere, and the mixture is stirred for four hours at 25°. The reaction mixture is poured into an ice-cold solution of sodium bicarbonate and the product is taken up in ethyl acetate, the solution is washed until neutral and extracted again and the organic phase is dried and evaporated in a waterpump vacuum. The residue is dissolved in a small amount of methylene chloride ahd chromatographed on 30 times the amount by weight of silica gel. Elution with a mixture of hexane/ethyl acetate (2:1) gives 9α-fluoro-17α,21-dihydroxy-16α-methyl-pregna-1,4,11-triene-3,20-dione 17,21-dipropionate, which after recrystallisation from dichloromethane/diethyl ether/hexane melts at 166°–168°; $[\alpha]_D = +22°$ (c = 0.482; CHCl$_3$).

EXAMPLE 4

0.4 ml of piperidinosulphur trifluoride are added, at room temperature, to a suspension of 1.35 g of 9α-fluoro-11β,17α,21-trihydroxy-16α-methyl-pregna1,4-diene-3,20-dione 21-propionate (Dexamethason 21-propionate) in 20 ml of absolute dioxane, under an argon atmosphere. A clear solution is obtained after 10 minutes and is stirred for 4½ hours at room temperature. Working up as in Example 3 gives pure 9α-fluoro-17α,21-dihydroxy-16α-methyl-pregna-1,4,11-triene-3,20-dione 21-propionate, which after recrystallisation from acetone/hexane melts at 189° (decomposition); $[\alpha]_D + 26°$ (C =0.499; CHCl$_3$).

EXAMPLE 5

3 ml of piperidinosulphur trifluoride are added, at room temperature, to a suspension of 3.0 g of 9α-fluoro-11β,17α,21-trihydroxy-16α-methyl-pregna1,4-diene-3,20-dione 17,21-ethyl-orthopropionate (Dexamethason ethyl-orthopropionate) in 30 ml of absolute dioxane, under an argon atmosphere, and the mixture is stirred. A clear solution results after 10 minutes and is stirred for a further one hour. The reaction mixture is poured into an ice-cold solution of sodium bicarbonate and the product is taken up in ethyl acetate and washed until neutral. The organic phase is dried and evaporated in a waterpump vacuum. The residue is chromatographed on 30 times the amount of silica gel using hexane/ethyl acetate (3:1) as the eluant. After recrystallisation from methylene chloride/diethyl ether/hexane, the resulting 9α-fluoro-17α,21-dihydroxy-16α-methyl-pregna-1,4,11-triene-3,20-dione 17,21-ethyl-orthopropionate melts at 175–176°; $[\alpha]_D + 38°$ (C =0.43; CHCl$_3$).

EXAMPLE 6

A solution of 35 mg of potassium carbonate in 1 ml of water and 1 ml of methanol is added to a solution, which has been cooled to 0°, of 50 mg of 9α-fluoro-17α21-dihydroxy-16α-methyl-pregna-1,4,11-triene-3,20-dione 21-propionate in 2 ml of methanol and the mixture is stirred for 30 minutes at 5°. The reaction solution is neutralised with 50% strength aqueous acetic acid and concentrated in a waterpump vacuum. The residue is taken up in ethyl acetate and the solution is washed with water, dried and aevaporated. The resulting crude product is purified by chromatography on silica gel using hexane/ethyl acetate (1:1) as the eluant and the single product fractions are crystallised iron methylene chloride/acetone/hexane. The resulting 9α-fluoro-17α,21-dihydroxy-16α-methyl-pregna-1,4,11-triene-3,20-dione melts at 207°–209°.

EXAMPLE 7

A solution of 70 mg of potassium carbonate in 1 ml of water and 1 ml of methanol is added to a solution, which has been cooled to 0°, of 50 mg of 9α-fluoro-17α,21-dihydroxy-16α-methyl-pregna-1,4,11-triene-3,20-dione 17,21-dipropionate in 2 ml of methanol and the mixture is stirred for 40 minutes at 5°. Working up of the reaction product and the subsequent chromatography are carried out analogously to Example 6. The resulting product is in every respect identical with the 9α-fluoro-17α,21-dihydroxy-16α-methyl-pregna-1,4,11-triene-3,20-dione described in Example 6.

EXAMPLE 8

A solution of 1.2 g of 9α-fluoro-17α,21-dihydroxy-16α-methyl-pregna-1,4,11-triene-3,20-dione 17,21-ethyl-orthopropionate in 40 ml of methanol is warmed to 45°, 2.5 ml of 2 N oxalic acid are added and the mixture is stirred for 30 minutes at 45°. The reaction mixture is cooled rapidly and poured into an ice-cold solution of potassium bicarbonate and the product is taken up in methylene chloride, washed with water and dried. The organic phase is evaporated and the residue is chromatographed on 20 times the amount of silica gel using hexane/ethyl acetate (1:1) as the eluant. Pure, amorphous 9α-fluoro-17α,21-dihydroxy-16α-methyl-pregna-1,4,11-triene-3,20-dione 17-propionate results; $[\alpha]_D = -10°$ (c =0.462; CHCl$_3$).

EXAMPLE 9

0.8 ml of propionic anhydride are added, at 0°, to a solution of 400 mg of 9α-fluoro-17α,21-dihydroxy-16αmethyl-pregna-1,4,11-triene-3,20-dione 17-propionate in 1.6 ml of prydiene and the mixture is stirred for two hours at 0°. 4 g of ice are added to the reaction mixture and the reaction mixture is stirred for a further one hour and then extracted with methylene chloride. The extracts are washed successively with hydrochloric acid, a sodium bicarbonate solution and water, dried and evaporated. The residue is chromatographed on 20 times the amount of silica gel using hexane/ethyl acetate (2:1). After recrystallisation from methylene chloride/diethyl ether/hexane, the resulting 9α-fluoro-17α,21-dihydroxy-16α-methyl-pregna-1,4,11triene-3,20-dione 17,21-dipropionate melts at 166-167°; [α]$_D$= +22° (c = 0.441; CHCl 3).

EXAMPLE 10

2.0 ml of piperidinosulphur trifluoride are added to a solution of 2.28 g of 9α-fluoro-11β,17α-dihydroxy-16α-methyl-3,20-dioxo-pregna-1,4-diene-21-al 17-propionate in 25 ml of absolute dioxane, at room temperature and under a nitrogen atmosphere, and the mixture is stirred for four hours at 25°. The reaction mixture is poured into an ice-cold solution of sodium bicarbonate and taken up in ethyl acetate. The organic phase is washed with saturated sodium chloride solution, dried and evaporated in a waterpump vacuum. The oily residue is chromatographed on 30 times the amount of silica gel and eluted with toluene/ethyl acetate (3:1). After recrystallisation from methylene chloride/diethyl ether/hexane, the resulting 9α-fluoro-17α-hydroxy-16α-methyl-3,20-dioxo-pregna-1,4,11-trien-21-al 17-propionate melts at 133°-138°; [α]$_D$+30° (c = 0.523; CHCl 3).

EXAMPLE 11

1.8 ml of piperidinosulphur trifluoride are added to a solution, which is stirred underr argon, of 2.0 g of 9α-fluoro-11β,17α,21-trihydroxy-16β-methyl-pregna-1,4-diene-3,20-dione 17-valerate-21-propionate (Betamethason 17-valerate-21-propionate) in 25 ml of dioxane. After 2¼ hours at 25°, the reaction mixture is poured into an ice-cold solution of sodium bicarbonate and extracted with methylene chloride. The organic phase is washed with water until neutral, dried and evaporated in a water pump vacuum. The resulting amorphous residue is chromatographed on silica gel and eluted with hexane/ethyl acetate (3:1). Afrer recrystallising once from methanol/water, the resulting pure 9α-fluoro-17α,21-dihydroxy-16β-methyl-pregna-1,4,11-triene-3,20-dione 17-valerate-21-porpionate melts at 119°-120°.

EXAMPLE 12

1.2 ml of piperidinosulphur trifluoride are added to a solution of 2.5 g of 6α,9α-difluoro-11β,17α,21-trihydroxy-16α-methyl-pregna-1,4-diene-3,20-dione 21-trimethyl-acetate (Flumethason 21-trimethyl-acetate) in 13 ml of absolute pyridine, at room temperature and under an argon atmosphere, and the mixture is stirred for 2 hours at room temperature. The reaction mixture is poured into ice water and extracted twice with ethyl acetate. The organic phase is washed until neutral, dried and evaporated in a waterpump vacuum. The residue is dissolved in pyridine, transferred to a column charged with 70 g of silica gel and washed out with hexane/ethyl acetate (3:1),. After recrystallisation from acetone/ethyl acetate, the resulting 6α,9α-difluoro-17α,21-dihydroxy- 16α-methyl-pregna-1,4,11-triene-3,20-dione 21-trimethyl-acetate mealts at 250°-252°; [α]$_D$+18° (c = 0.499; CHCl₃).

EXAMPLE 13

1.9 ml of piperidinosulphur trifluoride and added to a suspension of 2.61 g of 6α,9α-difluoro-11β,17α,21-trihydroxy-16α-methyl-pregna-1,4-diene-3,20-dione 17,21-dipropionate (Flumethason 17,21-dipropionate) in 50 ml of absolute dioxane, at room temperature and under a nitrogen atmosphere, and the mixture is stirred at room temperature. After about 20 minutes, all of the steroid has dissolved. After a reaction time of 3 hours, the reaction mixture is processed as indicated under Example 3. After recrystallisation from methylene chloride/diethyl ether/hexane, the resulting 6α,9α-difluoro-17α,21-dihydroxy-16α-methyl-pregna-1,4,11-triene-3,20-dione 17,21-dipropionate melts at 114°-116°; [α]$_D$+14° (C = 0.672; CHCl₃).

EXAMPLE 14

Piperidinosulphur trifluoride (1.5ml) is added to a suspension of 2.33 g of 6α,9α-difluoro-11β,21-dihydroxy-16α,17α-isopropylidenedioxy-pregna-Lb 1,4-diene-3,20-dione 21 -acetate in 35 ml of dioxane, whilst passing argon over the mixture and stirring. The starting material dissolves within 7 minutes. After a further 1½hours at room temperature, the reaction mixture is poured into an ice-cold solution of sodium bicarbonate and extracted with ethyl acetate. The organic extracts are washed twice with water, dried over sodium sulphate and concentrated in a waterpump vacuum. The oily crude product is purified by chromatography on fifty times the amount by weight of silica gel. The 11-piperidino-sulphinate of the starting material, which melts at 191°-194°, is first eluted with hexane/ethyl acetate (3:1) and the desired pure 6α,9α-difluoro-21-hydroxy-16α,17α-isopropylidenedioxy-pregna-1,4,11-triene-3,20-dione 21 -acetate is then eluted with hexane/ethyl acetate (2:1). After recrystallisation from acetone/hexane, the compound melts at 223°-225°, with decomposition; [α]$_D$= +47°(c=0.452; CHCl₃).

We claim:
1. Process for the manufacture of an 11,12-unsaturated 9α-fluoro-steroid, wherein a 9α-fluoro-11β-hydroxy-steroid is reacted with a compound of the formula F₃SX in which X denotes an amino group derived from a secondary amine.

2. Process according to claim 1, wherein the reaction is carried out with an aminosulphur trifluoride in which the amino group is di-lower alkylamino, unsubstituted or c-lower alkylated pyrrolidino, piperidino, morpholino or N'-lower alkylpiperazino.

3. Process according to claim 2, wherein the reaction is carried out with diethylaminosulphur trifluoride or perpendicular trifluoride.

4. Process according to claim 1, wherein, in order to protect the 17α,21-dihydroxy-20-oxo grouping, only any one of the two hydroxyl groups is esterified by a carboxylic acid which contains at least 3 carbon atoms.

5. Process according to claim 1 for the manufacture of a compound of the general formula t

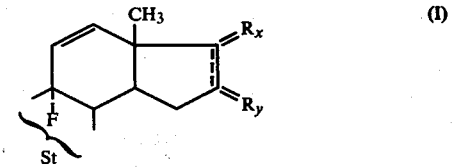

in which St represents the remaining part of the steroid molecule comprising the ring A and carbon atoms C-6, C-7, and C-19, which can carry one or more double bonds and be substituted by one or more substituents selected from the group consisting of tree, etherified and esterified hydroxyl, free and ketalized oxo, lower alkyl and halogen, R$_x$ denotes a member selected from the grou consisting of oxo, a ketalised oxo group, lower alkylidene, substituted lower alkylidene, hydrogen together with hydroxyl, etherified hydroxyl or esterified hydroxyl, a lower alphatic hydrocarbon radical together with hydroxyl, etherified hydroxyl or esterified hydroxyl, a substituted lower aliphatic hydrocarbon radical together with hydroxyl, etherified hydroxyl or esterified hydroxyl, hydrogen together with lower alkyl and hydrogen together with substituted lower alkyl, whereby the substituents of th said substituted alkylidene, alkyl and aliphatic hydrocarbon radicals or halogen atoms, free, esterified or etherified hydroxyl groups, free or ketalised oxo groups, and $R_y$ denotes a member selected from the group consisting of lower alkylidene, hydrogen together with hydroxyl, etherified hydroxyl or esterified hydroxyl, lower alkyl together with hydrogen, and two hydrogen atoms, it being possible for a 16, 17-double bond to be present in place of one of the said hydrogen atoms in radical $R_x$ and one of the said hydrogen atoms in racidal $R_y$, wherein a compound of the general formula II.

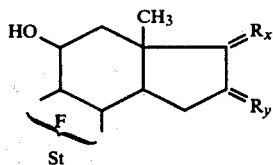

in which St, $R_x$ and $R_y$ have the above mentioned meaning, is dehydrated with a compound of the formula $R_3$ SX, wherein X denotes an amino group derived from a secondary amine, with the proviso that all hydroxyl groups present in any of the symbols St, $R_x$ and $R_y$ are temporarily protected by esterification.

6. Process according to claim 1, wherein the reaction is carried out with a starting material in which any free carboxyl and/or hydroxyl groups which may be present are temporarily protected.

7. Process according to claim 1 for the manufacture of an 11,12-unsaturated $9_\alpha$-fluoro-sterioid selected from the group consisting of a compound of the general formula IA

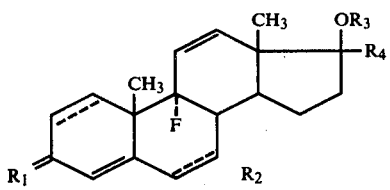

in which $R_1$ denotes oxo, hydrogen together with hydroxyl or hydroxyl esterified with a carboxylic acid with no more than 18 C-atoms, $R_2$ denotes hydrogen or methyl, $R_3$ denotes hydrogen, lower alkyl, cycloalkyl with 5 to 6 to ring-members, or acyl of a carboxylic acid with no more than 18 C-atoms and $R_4$ denotes hydrogen or a lower aliphatic hydrocarbon radical, or $OR_3$ and $R_4$ conjointly represent oxo, and an additional double bond can be present in the 1,2-position and/or the 6,7-position, and of a comppound of the general formula IB.

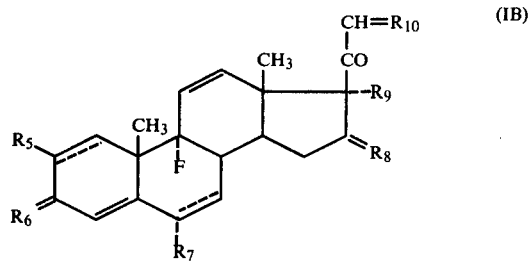

in which $R_5$ is hydrogen, alpha-oriented methyl or, with the provisothat a 1,2-double bond is present, chlorine, $R_6$ is oxo or hydrogen together with hydroxyl, $R_7$ is hydrogen, methyl or halogen, $R_8$ is two hydrogen atoms, methylene, hydrogen together with alpha- or beta- oriented methyl or hydrogen together with alpha-oriented hydroxyl, $R_9$ is hydrogen, hydroxyl or hydroxyl esterified with a lower alkane carboxylic or orthocarboxylic acid and $R_{10}$ is two hydrogen atoms, two hydroxyls, oxo, or acetalised oxo, or hydrogen together with hydroxyl or hydroxyl esterified with a carboxylic acid with not more than 18 C-atoms, and in which compound a double bond can be present in both the 1,2-position and/or the 6,7-position and ketals or acetals or all such compounds in which a 16,17 alpha-diol grouping is present together with an oxo compound of the formula $R_{11}$—CO—$R_{12}$, in which $R_{11}$ and $R_{12}$ each denotes hydrogen, lower alkyl, phenyl or benzyl, or cojointly denote tetramethylene or pentamethylene, in which process a 11,12-saturated $9\alpha$-fluoro-$11\beta$-hydroxy-steroid which is structurally corresponding to the above defined compounds of formula IA and IB is treated with an aminosulphur trifluoride of the formula $F_3SX$, in which X denotes an amino group derived from a secondary amine.

8. A compound according to claim 1 selected from the group consisting of $9\alpha$-fluoro-$17\beta$-hydroxy-$17\alpha$-methyl-androsta-4,11-dien-3-one and its 17-trifluoroacetate.

9. A 9 alpha-fluoro-$\Delta^{11}$-steroid, which has the general formula IA

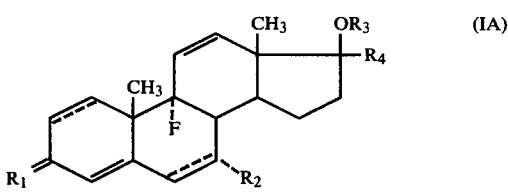

in which $R_1$ denotes oxo, hydrogen together with hydroxyl or hydroxyl esterified with a carboxylic acid with no more than 18 C-atoms, $R_2$ denotes hydrogen or methyl, $R_3$ denotes hydrogen, lower alkyl, cycloalkyl with 5 to 6 ring-members, or acyl of a carboxylic acid with no more than 18 C-atoms and $R_4$ denotes hydrogen or a lower aliphatic hydrocarbon radical, or $OR_3$ and $R_4$ conjointly represent oxo, and an additional double bond can be present in the 1,2-position and/or the 6,7-position.

10. A 9 alpha-fluoro-$\Delta^{11}$-steroid according to claim 9 of the formula IA, in which $R_1$ is oxo, $R_2$ is hydrogen, $R_3$ is hydrogen or alkanoyl with 2 to 12 carbon atoms and $R_4$ is hydrogen or methyl, and the 1,2-dehydro-derivative thereof.

11. A 9 alpha-fluoro-Δ¹¹-steroid according to claim 9 of the formula IA, in which $R_1$ is oxo, $R_2$ is hydrogen, $R_3$ is lower alkanoyl or hydrogen and $R_4$ is an unsaturated hydrocarbon radical with 1-4 C atoms, and which can also carry a double bond in the 1,2-position and/or in the 6,7-position.

12. A 9 alpha-fluoro-Δ¹¹-steroid which has the general formula IB

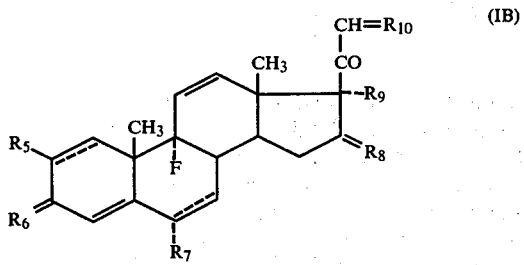

in which $R_5$ is hydrogen, alpha-oriented methyl or, with the proviso that a 1,2-double bond is present, chlorine, $R_6$ is oxo or hydrogen together with hydroxyl, $R_7$ is hydrogen methyl or halogen, $R_8$ is two hydrogen atoms, methylene, hydrogen together with alpha- or beta- oriented methyl or hydrogen together with alpha-oriented hydroxyl, $R_9$ is hydrogen, hydroxyl or hydroxyl esterified with a lower alkane carboxylic acid or orthocarboxylic acid and $R_{10}$ is two hydrogen atoms, two hydroxyls, oxo, or acetalised oxo, or hydrogen together with hydroxyl or hydroxyl esterified with a carboxylic acid with not more than 18 C-atoms, and in which compound a double bond can be present in mboth the 1,2-position and/or the 6,7-position and ketals or acetals of all such compounds in which a 16,17 alpha-diol grouping is present together with an oxo compound of the formula $R_{11}$—CO—$R_{12}$, in which $R_{11}$ and $R_{12}$ each denotes hydrogen, lower alkyl, phenyl or benzyl, or conjointly denote tetramethylene or pentamethylene, with the proviso that in compounds in which $R_9$ is hydroxyl and $R_{10}$ is hydrogen together with hydroxyl, only one of both hydroxyls is in the free form.

13. A 9 -alpha-fluoro-Δ¹¹-steroid according to claim 12 of the formula IB, in which $R_5$ is hydrogen or, with the proviso that a 1,2-double bond is present, chlorine, $R_6$ is oxo, $R_7$ is hydrogen, methyl or fluorine, $R_8$ stands for two hydrogens or hydrogen together with methyl, $R_9$ is hydroxyl or hydroxyl esterified with a lower alkane carboxylic or orthocarboxylic acid and $R_{10}$ is hydrogen together with hydroxyl or hydroxyl esterified with a lower alkane carboxylic or ortho-carboxylic acid, with the proviso that at least one of the hydroxyls in said two symbols is esterified, and the corresponding 1,2-dehydro-derivative thereof.

14. A 9 alpha-fluoro-Δ¹¹-steroid according to claim 12, in which $R_5$ is hydrogen, $R_6$ is oxo, $R_7$ is hydrogen or fluorine, $R_{10}$ is hydrogen together with hydroxyl or lower alkanoyloxy, $R_8$ denotes hydrogen together with an alpha-oriented hydroxyl and $R_9$ denotes hydroxyl, whereby both last mentioned hydroxyls together are ketalized with a dilower alkyl ketone, cyclopentanone, cyclohexanone or acetophenone, and the corresponding 1,2-dehydro derivative thereof.

15. A 9 alpha-fluoro-≠¹¹ -steroid according to claim 14, wherein the ketonic component is acetone.

16. A 9 alpha-fluoro-Δ¹¹-steroid according to claim 12, in which $R_5$ is hydrogen or, with the proviso that a 1,2-double bond is present, chloro, $R_6$ is oxo, $R_7$ is hydrogen or fluorine, $R_8$ stands for two hydrogens or hydrogen together with alpha-oriented methyl, $R_9$ is hydrogen, and $R_{10}$ is oxo or hydrogen together with hydroxyl or with lower alkanoyloxy, and the corresponding 1,2-dehydro-derivative thereof.

17. A 9 alpha-fluoro-Δ¹¹-steroid according to claim 12, of the formula IB, in which $R_5$ is hydrogen, $R_6$ is oxo, $R_7$ is hydrogen, chlorine or methyl, $R_8$ stands for two hydrogens, $R_9$ is hydrogen, hydroxyl or lower alkanoyloxy and $R_{10}$ represents two hydrogen atoms, and a corresponding 6,7-dehydroderivative thereof.

18. A compound according to claim 12, selected from a group which consists of the following compounds: 9α-fluoro-17α,21-dihydroxy-16α-methyl-pregna-1,4,11-triene-3,20-dione and its 17-propionate; 21-propionate; 17,21-dipropionate and 17,21-ethyl-orthoprionate; 9α-fluoro-17α-hydroxy-16α-methyl-3,20-dioxo-pregna-1,4,11-trien-21-al 17-propionate; 9α-fluoro-17α,21-dihydroxy-16 ↑ -methyl-pregna-1,4,11-triene-3,20 -dione 17-valerate-21-propionate; 6α,9α-difluror-17α,21 -dihydroxy-16α-methyl-pregna-1,4,11-triene-3,20-dione in the form of its 21-trimethylacetate an 17,21-dipropionate and 6α,9α-difluoro-21-hydroxy-16α,17α-isopropylidenedioxy-pregna-1,4,11-triene-3,20-dione 21-acetate.

* * * * *